(12) United States Patent
Zimmer

(10) Patent No.: US 6,592,815 B1
(45) Date of Patent: Jul. 15, 2003

(54) ANALYTICAL TEST ELEMENT WITH A NARROWED CAPILLARY CHANNEL

(75) Inventor: Volker Zimmer, Dossenheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/554,842

(22) PCT Filed: Dec. 3, 1998

(86) PCT No.: PCT/EP98/07853

§ 371 (c)(1),
(2), (4) Date: Sep. 19, 2000

(87) PCT Pub. No.: WO99/30158

PCT Pub. Date: Jun. 17, 1999

(30) Foreign Application Priority Data

Dec. 4, 1997 (DE) .......................................... 197 53 849

(51) Int. Cl.[7] .............................................. G01N 21/00
(52) U.S. Cl. .............................. 422/58; 422/55; 422/56; 436/169
(58) Field of Search .............................. 422/58, 50, 55, 422/56, 57; 436/63, 169, 170

(56) References Cited

U.S. PATENT DOCUMENTS

| 4,477,575 A | 10/1984 | Vogel et al. ................. 436/170 |
| 4,529,480 A | * 7/1985 | Trokhan ....................... 162/109 |
| 4,696,797 A | * 9/1987 | Kelton .......................... 422/101 |
| 4,849,340 A | * 7/1989 | Oberhardt ....................... 435/13 |
| 5,055,195 A | * 10/1991 | Trasch .......................... 210/638 |
| 5,423,989 A | * 6/1995 | Allen et al. ................... 210/650 |
| 5,814,522 A | 9/1998 | Zimmer et al. ............... 436/170 |

FOREIGN PATENT DOCUMENTS

| DE | 31 51 291 A1 | 8/1982 | .......... G01N/33/48 |
| DE | 195 23 049 A1 | 1/1997 | .......... G01N/31/22 |
| EP | 0 045 476 A1 | 2/1982 | .......... G01N/33/48 |
| EP | 0 215 419 A2 | 3/1987 | ............ G01N/1/00 |
| GB | 1 264 433 | 2/1972 | ............ B44D/1/22 |

* cited by examiner

*Primary Examiner*—Jill Warden
*Assistant Examiner*—Sam P. Siefke
(74) *Attorney, Agent, or Firm*—Jill L. Woodburn

(57) ABSTRACT

The invention concerns an analytical test element for the determination of an analyte in a liquid containing a detection element and a channel capable of capillary liquid transport which has a sample application opening at one end of the channel capable of capillary liquid transport, wherein the channel capable of capillary liquid transport is continuously narrowed from the sample application opening in the direction of capillary transport at least up to the beginning of the detection element. In addition it also concerns the use of the said analytical test element for the determination of an analyte in a liquid as well as a method for determining an analyte in a liquid sample with the aid of the said analytical test element.

15 Claims, 1 Drawing Sheet

ANALYTICAL TEST ELEMENT WITH A NARROWED CAPILLARY CHANNEL

The invention concerns an analytical test element for the determination of an analyte in a liquid containing a detection element and a channel capable of capillary liquid transport which has a sample application opening at one end of the channel capable of capillary liquid transport. The invention also concerns the use of the said analytical test element for the determination of an analyte in a liquid as well as a method for the determination of an analyte in a liquid sample with the aid of the said analytical test element.

So-called carrier-bound tests are often used for the qualitative or quantitative analytical determination of components of body fluids, in particular of blood. In these the reagents are contained in corresponding layers of a solid carrier which is contacted with the sample. If a target analyte is present, the reaction of the liquid sample and reagents leads to a detectable signal, in particular a colour change, which can be evaluated visually or with the aid of an instrument, usually by reflection photometry.

Test elements or test carriers are often in the form of test strips which are essentially composed of an elongate support layer made of plastic material and detection layers which are applied thereto as test fields. However, test carriers are also known which are in the shape of small quadratic or rectangular plates. Test elements for clinical diagnostics that are evaluated visually or by reflection photometry are frequently constructed such that the sample application zone and the detection zone are arranged one above the other in a vertical axis. This mode of construction is problematic. When the test strip loaded with sample has to be inserted into an instrument, for example a reflection photometer, for measurement, potentially infectious sample material can come into contact with parts of the instrument and may contaminate them. Furthermore volumetric dosing can only be achieved with difficulty especially in cases in which the test strips are used by untrained persons for example in the self-control of blood sugar by diabetics. Moreover conventional test elements often require relatively large sample volumes due to their construction in order to enable reliable measurements. The more sample volume is required, the more painful this can be for the patient whose blood is to be examined. It is therefore a general goal to provide test strips which require as little sample material as possible.

An instrument for the analysis of biological fluids is known from DE-A 31 51 291 which has a carrier with a self-filling measurement channel as well as a laminate arrangement containing a filter layer and a reagent material layer. In this test carrier the sample liquid is transported into the measurement channel by capillary forces and from this it penetrates into the overlying laminate where a detection reaction for the target analyte takes place after heating the analytical instrument. A disadvantage is that the analytical instrument with the sample contained therein must be heated to achieve a measurement result. As a result the use of the analytical instrument is essentially limited to laboratories.

In DE-A 195 23 049 a multilayer analytical element is described containing a sample application zone and a detection zone arranged next to one another. The multilayer analytical element is essentially composed of a sandwich of a fleece and a porous membrane which are in a contact enabling liquid transfer over the whole area and in which the membrane and the sample application zone is treated in such a way that it does not take up or transport liquid in this area. The multilayer analytical element from DE-A 195 23 049 can be used in a test strip which contains a capillary gap by which means the sample liquid can be contacted with the sample application zone.

The object of the present invention was to eliminate the disadvantages of the prior art. In particular it was intended to provide a simple to handle test element that can automatically dose volumes and enables a spatial separation of the detection zone and sample application site while using minimal sample volumes. In addition the sample transport from sample application to the detection zone should be so rapid that this does not limit the time required to analyse a sample. Furthermore a simple construction of the test element should enable the test element to be manufactured cost-effectively and simply.

This is achieved by the subject matter of the invention as characterized in the patent claims.

The subject matter of the invention is an analytical test element for the determination of an analyte in a liquid containing a detection element and a channel capable of capillary liquid transport which has a sample application opening at one end of the channel capable of capillary liquid transport characterized in that the channel capable of capillary liquid transport is continuously narrowed from the sample application opening in the direction of capillary transport at least up to the beginning of the detection element.

The narrowing of the capillary-active channel serves to ensure that the sample volume located in the capillary channel can be reliably absorbed by the detection element without separation of the column of sample liquid. The risk with a channel that becomes narrower is that the liquid column is disrupted when the sample liquid is transferred from the inside of the channel onto the detection element, only part of the liquid in the capillary-active channel reaches the detection element and hence an underdosage of the detection zone results. This is counteracted by the narrowing according to the invention. The narrowing of the channel capable of capillary liquid transport preferably relates to that dimension of the channel which causes its capillarity. For capillaries with a rectangular cross-section this is usually the height of the channel. In this connection the height of the channel is that dimension that forms a right angle with the direction of transport of liquid in the channel and furthermore is essentially perpendicular to the plane of the detection element which is exposed for observation or measurement. In contrast to the height, the width of the channel is essentially parallel to the said plane of the detection element. The continuous narrowing of the channel towards the detection element also continuously increases the capillarity. If sample liquid now passes from the channel into the detection element, the higher capillarity in the channel on the side of the detection element causes sample liquid to move up from the regions of lower capillarity. In this manner a complete filling of the detection element is achieved which is associated with an—in the ideal case complete—emptying of the channel. Therefore no more sample has to be taken up into the channel than is required for the detection element.

In a preferred embodiment the narrowing of the channel capable of capillary liquid transport is linear from the sample application opening to the detection element. However, other forms of narrowing are also conceivable such as a slightly curved variant. In other words this means that the cross-section of the capillary-active channel at the sample application opening is larger than at the opposite end of the channel which is located under the detection element.

It is particularly preferred that the channel capable of capillary liquid transport is terminated at the opposite end to the sample application opening by an abrupt widening of that dimension of the channel which causes its capillarity. Such an abrupt widening can also be referred to as a height step.

The channel capable of capillary liquid transport preferably extends in the direction of capillary transport from the sample application opening to at most the border of the detection zone of the detection element that faces the sample application opening. In a particularly preferred embodiment the dimensions of the capillary channel are matched to the detection element in such a way that the maximum sample volume which the capillary channel can take up corresponds approximately to the amount of sample that can be absorbed by the detection element and is necessary for a reliable analysis. In the ideal case both volumes are of equal size and the sample is completely transferred from the channel into the detection element. This prevents excess sample from reaching the detection element and also avoids too little sample being available for the detection reaction. Since the detection reaction and the signals resulting therefrom are volume-dependent beyond certain system limits, underdosing or overdosing leads to erroneous measured results. These are avoided by the method according to the invention. Hence the capillary channel has the purpose of volume dosing through the test element with the goal of avoiding underdosing or overdosing of the detection element and thus preventing unreliable or even false measured results.

Since, in the preferred case that the channel has an essentially rectangular cross-section, one dimension, for example the height of the channel, is preset by the physical limits of capillary activity, the volume of the capillary channel can be adjusted by suitable selection of the two other dimensions for example length and width. The height of the capillary is for example for blood of the order of magnitude of 10 to 500 $\mu$m, preferably between 20 and 300 $\mu$Am since otherwise no capillary activity is observed. For the narrowed channel this applies to the height on the sample application side as well as on the opposite side that faces the detection element. Depending on the desired volume the width can then be several mm preferably 1 to 10 mm and the length can be up to several cm, preferably 0.5 to 5 cm.

In a preferred embodiment of the analytical test element according to the invention at least one, but preferably two and especially preferably two opposite surfaces which form the inner surface of the channel capable of capillary liquid transport are hydrophilized. In this connection hydrophilic surfaces are water-attracting surfaces. Aqueous samples, also including blood, spread well on such surfaces. Such surfaces are characterized among others in that a water drop placed on it forms an acute rim angle or contact angle at the interface. In contrast an obtuse rim angle is formed at the interface between the water drop and the surface on hydrophobic i.e. water repellent surfaces.

The rim angle which is a result of the surface tensions of the test liquid and of the surface to be examined is suitable as a measure of the hydrophilicity of a surface. Water for example has a surface tension of 72 mN/m. If the value of the surface tension of the observed surface is much below this value i.e. more. than 20 mN/m under this value, then the wetting is poor and the resulting rim angle is obtuse. Such a surface is referred to as hydrophobic. If the surface tension approximates the value which is found for water then the wetting is good and the rim angle is acute. If, in contrast, the surface tension is the same as or higher than that of the value found for water, then the drop runs and there is a total spreading of the liquid. It is then no longer possible to measure a rim angle. Surfaces which form an acute rim angle with water drops or on which a total spreading of a water drop is observed are referred to as hydrophilic.

The ability of a capillary to suck up a liquid depends on the wettability of the channel surface with the liquid. This means for aqueous samples that a capillary should be manufactured from a material whose surface tension almost reaches 72 mN/m or exceeds this value.

Sufficiently hydrophilic materials for the construction of a capillary which rapidly sucks up aqueous samples are for example glass, metal or ceramics. However, these materials are unsuitable for use in test carriers since they have some severe disadvantages such as risk of breaking in the case of glass or ceramics or change in the surface properties with time in the case of numerous metals. Therefore plastic foils or moulded parts are usually used to manufacture test elements. As a rule the plastics used hardly exceed a surface tension of 45 mN/m. Even with the, in a relative sense, most hydrophilic plastics such as polymethylmethacrylate (PMMA) or polyamide (PA) it is only possible—if at all—to construct slowly sucking capillaries. Capillaries made of hydrophobic plastics such as for example polystyrene (PS), polypropylene (PP) or polyethylene (PE) essentially do not aspirate aqueous samples. Consequently it is necessary to endow the plastics used as a construction material for test elements with capillary active channels with hydrophilic properties i.e. to hydrophilize them.

As already mentioned above in a preferred embodiment of the analytical test element according to the invention at least one, but preferably two and especially preferably two opposite surfaces which form the inner surface of the channel capable of capillary liquid transport are hydrophilized. If more than one surface is hydrophilized then the surfaces can either be made hydrophilic using the same or different methods. Hydrophilization is particularly necessary when the materials that form the capillary active channel, in particular the carrier, are themselves hydrophobic or only very slightly hydrophilic because they are for example composed of nonpolar plastics. Nonpolar plastics such as for example polystyrene (PS), polyethylene (PE), polyethylene terephthalate (PET) or polyvinyl chloride (PVC) are advantageous as carrier materials because they do not absorb the liquids to be examined and thus the sample volume can be effectively utilized by the detection layer. The hydrophilization of the surface of the capillary channel enables a polar, preferably aqueous, sample liquid to readily enter the capillary channel and be rapidly transported there to the detection element or to the site of the detection element where the detection takes place.

Ideally the hydrophilizaton of the surface of the capillary channel is achieved by using a hydrophilic material for its manufacture which, however, cannot itself aspirate the sample liquid or only to a negligible extent. In cases where this is not possible a hydrophobic or only very slightly hydrophilic surface can be hydrophilized by suitable coating with a stable hydrophilic layer that is inert towards the sample material for example by covalently binding photo-reactive hydrophilic polymers onto a plastic surface by applying layers containing wetting agents or by coating surfaces with nanocomposites by means of sol-gel technology. Furthermore it is also possible to achieve an increased hydrophilicity by thermal, physical or chemical treatment of the surface.

The hydrophilization is quite especially preferably achieved by using thin layers of oxidized aluminium. These layers are either applied directly to the desired components of the test element for example by vacuum coating the work pieces with metallic aluminium and subsequently oxidizing the metal, or by using metal foils or metal-coated plastics for the construction of the test carriers which also have to be oxidized to achieve the desired hydrophilicity. In this case metal layer thicknesses of 1 to 500 nm are adequate. The metal layer is subsequently oxidized to form the oxidized form in which case above all oxidation in the presence of water vapour or by boiling in water have proven to be especially suitable methods in addition to electrochemical, anodic oxidation. The oxide layers formed in this manner are between 0.1 and 500 nm, preferably between 10 and 100 nm thick depending on the method. Larger layer thicknesses of the metal layer as well as of the oxide layer can in principle be realised in practice but do not exhibit any additional advantageous effects.

In a preferred embodiment the detection element of the analytical test element according to the invention contains all reagents required for the detection reaction of the target analyte in the sample and optionally auxiliary substances. However, it is also possible that only parts of the reagents or auxiliary substances are contained. Such reagents and auxiliary agents are well-known to an expert familiar with the technology of analytical test elements or diagnostic test carriers. For analytes that are detected enzymatically, the detection element can for example contain enzymes, enzyme substrates, indicators, buffer salts, inert fillers etc.

The detection element of the test element according to the invention is preferably composed of several layers and can optionally contain an inert carrier, preferably on the side of the detection element that is not contacted with the sample. In the particularly preferred case that the detection reaction leads to an observable change in colour which in this connection is understood as either a change of colour, formation of a colour or disappearance of colour, it must be ensured by suitable measures that the carrier allows a visual or optical observation of the detection reaction. For this purpose the carrier material of the detection element can itself be transparent for example a transparent plastic foil such as a polycarbonate foil or have a transparent recess on the detection side. In addition to detection reactions that lead to colour changes, other detection principles are also known to a person skilled in the art which can be realised with the described test element such as electrochemical sensors.

It is necessary for the detection element that materials are used which are able to take up the liquid to be examined with the constituents contained therein. These are so-called absorbent materials such as for example fleeces, fabrics, knitted fabrics or porous plastic materials which can be used as layer materials. Suitable materials must be able to carry reagents that are required for the detection of the analyte to be determined.

Preferred materials for the detection element are fleeces, papers or porous plastic materials such as membranes. Polyamide, polyvinylidene difluoride, polyethersulfone or polysulfone membranes are especially preferred as porous membrane materials. The reagents for the determination of the analyte to be detected are usually incorporated in the above-mentioned materials by impregnation.

A particularly preferred detection element is a multilayer, stack-like material sandwich containing a sample application zone and a detection zone arranged next to one another in which the detection zone contains a reagent which forms a detectable signal with the analyte to be determined or with a substance derived therefrom. The sample application and detection zone are arranged on a stack-like sandwich of a fleece and a porous membrane in such a way that they are in direct or indirect contact enabling a planar liquid transfer. The membrane is selected such that it transports liquid horizontally, i.e. over an area, considerably more slowly than the fleece. In the region of the sample application zone which extends up to the detection zone of the multilayer analytical element, the membrane is treated such that it neither absorbs nor transports liquid. This ensures that firstly the sample can completely impregnate the fleece from the sample application zone and only subsequently penetrates into the membrane. Such detection elements are known from DE-A 195 23 049. The detection elements described there are used especially preferably for the test element according to the invention. Of course the detection zone of the detection element can also be composed of several discrete zones which are suitable for the detection of different target analytes from a sample liquid.

Detection elements as described in DE-A 195 23 049 are equipped with components which exclude interfering sample components from the detection reaction and thus act as filters for example for particulate sample components such as blood cells. For example when analysing blood samples the red blood pigment haemoglobin which is present in the red blood corpuscles (erythrocytes) can interfere with visual or optical detection methods. It is expedient to separate these interfering components from the sample, for example whole blood, before the actual detection reaction. This can be achieved by sample preparation before applying the sample to the test element such as by centrifuging whole blood and subsequently isolating the serum or plasma. It is more convenient and also simpler for a layman if the test element itself carries out this separation step by means of a suitable construction. A person skilled in the art knows means from test strip technology which ensure a reliable exclusion of erythrocytes. Examples are the use of semipermeable membranes or glass fibre fleeces to separate red blood corpuscles as known for example from EP-B-0 045 476.

In addition to the already mentioned advantages of the test element according to the invention it also has other merits. The spatial separation of the sample application site and signal detection in conjunction with the sample volume dosing enables the sample material to be handled hygienically. Especially in the case of optical detections for example with the aid of a reflection photometer, contamination of the instrument is largely ruled out since the sample can for example be applied to a test element which protrudes from the instrument, is completely aspirated into the capillary channel and automatically transported without further measures to the detection zone of the test element located inside the instrument. Moreover the complete aspiration of the sample material by the capillary-active zone in the test element prevents excess sample from remaining on the outside of the test element so that this property also contributes to hygiene.

Furthermore the test element according to the invention requires considerably less sample material than conventional test elements in a quite especially preferred embodiment. Whereas the latter often require more than 12 $\mu$l sample liquid, the required minimum sample volume for the test element according to the invention is reduced to considerably less than 10 $\mu$l, preferably less than 5 $\mu$l and particularly preferably 3 to 4 $\mu$l sample. This is achieved by optimization of the sample flow exactly to the site of determination as well as by the fact that the sample volume can be transferred almost quantitatively from the channel into the detection element which in turn is due to its diminishing cross-section. Especially in the case that the sample is blood, this can simplify sample collection for the person being examined and above all be associated with less pain.

A further subject matter of the invention is the use of an analytical test element according to the invention for the determination of an analyte in a liquid.

In addition the invention concerns a method for the determination of an analyte in a liquid sample, in particular a body fluid such as blood, plasma, serum, urine, saliva, sweat etc., with the aid of an analytical test element according to the invention. In this process the liquid sample is firstly contacted with the test element at the sample application opening. The sample liquid is transported by capillary forces into the channel that is capable of capillary liquid transport until it is completely filled. In this process the sample wets the surface of the detection element that faces the channel and penetrates into this. Optionally an analyte-specific detection reaction occurs between the sample and the reagents contained in the detection element which can be observed visually or optically by apparative means preferably by reflection photometry thus enabling conclusions to be drawn about the presence and optionally the amount of the analyte to be determined.

The invention is elucidated in more detail by FIGS. 1 and 2 and by the following examples.

Figure 1:
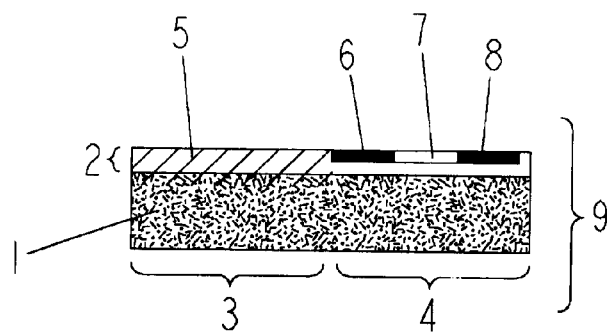
FIG. 1 shows a longitudinal section through a particularly preferred embodiment of the multilayer detection element.

1 carrier
2 membrane
3 sample application opening
4 detection zone
5 liquid-impermeable region
6 zone 1 containing reagents
7 zone 2 containing reagents
8 zone 3 containing reagents
9 multilayer detection element
10 cover
11 base part
12 sample application opening
13 vent opening
14 capillary-active region
15 height step A multilayer detection element (9) composed of a fleece (1) and membrane (2) for the parallel detection of three analytes is shown in FIG. 1. The sample application zone (3) extends over the region which is defined by the liquid impermeable region (5) of the membrane (2). Hence liquid which is applied to the fleece in the sample application zone (3) is in any case prevented by the liquid impermeable region (5) from penetrating there into the membrane (2). A passage of liquid from the fleece (1) into the membrane (2) is only possible within the detection zone (4). Appropriate selection of materials can ensure that the liquid applied to the fleece (1) in the sample application zone (3) rapidly disperses within the fleece (1) and from there passes transversely to the spreading direction in the fleece area into the detection zone (4) of the membrane (2) and there enters the zones (6,7,8) containing reagents. If the respective analyte is present a signal is formed in these zones which can be observed visually or by means of an instrument from the membrane side.

Figure 2:
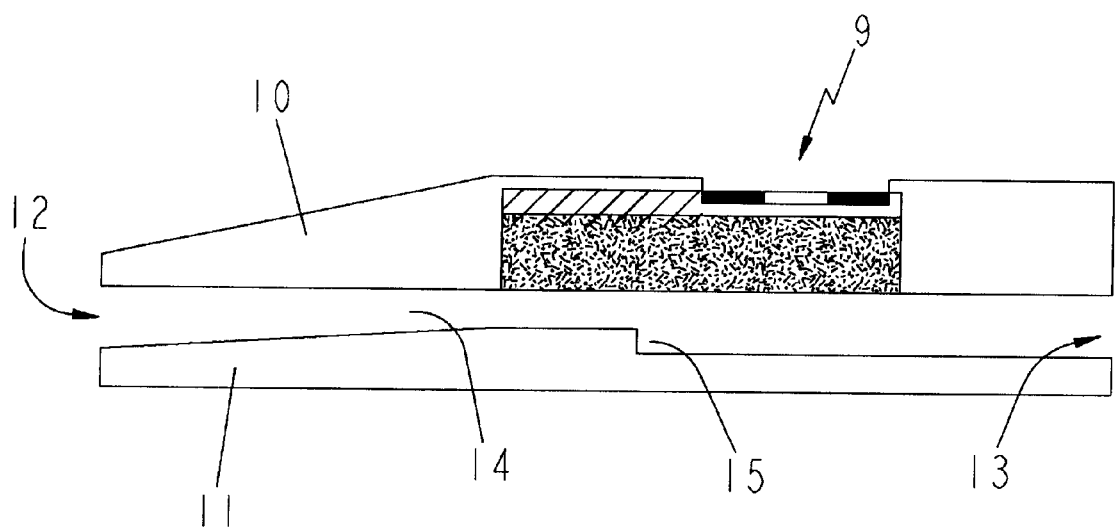
FIG. 2 shows a longitudinal section through a particularly preferred embodiment of a test element according to the invention.

FIG. 2 shows schematically a particularly preferred embodiment of the test element according to the invention. The test element is composed of a base part (11) manufactured by injection moulding and a likewise injection moulded cover (10) in which the detection element (9) is integrated. The injection moulded parts (10 and 11) can be clipped, welded or glued together. The shape and size of the capillary channel (14) are determined by the components base part (11), cover (10) and detection element (9). In particular the base part (11) determines the continuous narrowing and together with the height step (15) determines the length of the capillary-active channel (14). Alternatively the narrowing can also be determined by the cover (10) or by both.

A vent opening (13) is located on the opposite side of the sample application opening (12) of the capillary channel (14) which allows air to escape when the capillary channel (14) is filled with sample liquid.

The capillary zone (14) extends from the sample application opening (12) at most to the start of the detection zone of the multilayer detection element (9). The sample application opening (12) and height step (15) limit the capillary active region (3) in the direction of capillary transport.

When using the test element shown, the sample application opening (12) of the test element is for example contacted with a blood drop located on a fingertip. In this process the blood drop comes into contact with the capillary channel (14). The latter fills itself with sample until it is filled from the sample application opening (12) to the height step (15). Afterwards the test carrier is removed from the patient's finger which ensures that only the sample that is present in the capillary channel (14) is available for the detection element (9). Hence overdosing is prevented.

EXAMPLE 1

Manufacture of the analytical test element according to the invention

The base part (11) incorporating a recess which should result in the narrowing capillary channel, and the cover (10) which contains a recess for the detection element are manufactured from polymethylmethacrylate (PMMA) by means of an injection moulding process. Those surfaces of the injection moulded parts which come into contact with the sample liquid are subsequently vapour-coated in a vacuum coater with a layer of aluminium of a layer thickness of ca. 30 nm. Subsequently the aluminium layers are oxidized by treatment with hot water vapour.

A detection element (9) of a size fitting the recess, which was manufactured according to DE-A 195 23 049, was placed in the correct orientation in the coated cover (10). Subsequently the cover (10), which contains the detection element (9), and the base part (11) are glued together.

EXAMPLE 2

Measurement of the blood glucose concentration with the aid of the test element from example 1

The sample application side of the test element from example 1 is placed on a drop of sample liquid. The capillary of the test element automatically fills with sample within 2 s. If glucose is present in the sample a colour development is visible in the detection film after a few seconds. The end point of the reaction is reached after ca. 30 to 35 s. The colour obtained can be correlated with the glucose concentration of the sample and either evaluated visually or by reflection photometry.

What is claimed is:

1. Analytical test element for the determination of an analyte in a liquid, the test element comprising:
   a detection element and
   a channel capable of capillary liquid transport, the channel having a sample application opening at one end capable of capillary liquid transport and wherein the channel is continuously narrowed from the sample application opening in the direction of capillary transport at least up to the beginning of the detection element, wherein at least one of the surfaces that form the inner surface of the channel capable of capillary liquid transport is hydrophilized, the hydrophilization is achieved by using a hydrophilic material or by coating a material which is only slightly hydrophilic with a hydrophilic layer, and a layer of oxidized aluminium is used for hydrophilization.

2. Analytical test element for the determination of an analyte in a liquid, the test element comprising:

a detection element, a base, and a cover, the base and cover spaced-apart from one another a distance sufficient to create a capillary channel capable of capillary liquid transport, the channel having a sample application opening at one end capable of capillary liquid transport and wherein the channel is continuously narrowed from the sample application opening in the direction of capillary transport at least up to the beginning of the detection element, wherein the narrowing of the channel capable of capillary liquid transport relates to that dimension of the channel that causes its capillarity.

3. Analytical test element as claimed in claim 2, wherein the channel capable of capillary liquid transport is linearly narrowed.

4. Analytical test element as claimed in claim 2, wherein the channel capable of capillary liquid transport is terminated at the opposite end to the sample application opening by an abrupt widening of that dimension of the channel which causes its capillarity.

5. Analytical test element as claimed in claim 2, wherein at least one of the surfaces that form the inner surface of the channel capable of capillary liquid transport is hydrophilized.

6. Analytical test element as claimed in claim 5, wherein the hydrophilization is achieved by using a hydrophilic material or by coating a material which is only slightly hydrophilic with a hydrophilic layer.

7. Analytical test element as claimed in claim 2, wherein the detection element is a multilayer detection element having a sample application zone and a detection zone arranged adjacent to one another in which the detection element is arranged in the test element such that only the sample application zone is in contact enabling liquid transfer with the channel capable of capillary liquid transport.

8. Analytical test element as claimed in claim 7, wherein the multilayer detection element comprises at least one layer of reagent for the detection reaction of the target analyte in the sample.

9. Analytical test element as claimed in claim 7, wherein the multilayer detection element contains means for filtering particulate sample components.

10. Analytical test element as claimed in claim 7, wherein the multilayer detection element comprises a fleece and a porous membrane that are arranged in a stack-like sandwich such that planar liquid transfer is possible.

11. A method for determining an analyte in a liquid sample, the method comprising the steps of:

providing an analytical test element for the determination of an analyte in a liquid, the test element including a detection element, a base, and a cover, the base and cover spaced-apart from one another a distance sufficient to create a capillary channel capable of capillary liquid transport, the channel having a sample application opening at one end capable of capillary liquid transport, wherein the channel is continuously narrowed from the sample application opening in the direction of capillary transport at least up to the beginning of the detection element, wherein the narrowing of the channel capable of capillary liquid transport relates to that dimension of the channel that causes its capillarity, contacting the test element with a liquid sample at the sample application opening so that the liquid sample is transported by capillary forces into the channel until the liquid sample wets and penetrates the surface of the detection element that faces the channel in the region of the sample application zone, and observing the liquid sample in the detection element to draw conclusions about the presence of the analyte in the liquid sample.

12. The method of claim 11, further comprising the steps of providing at least one reagent in the detection element and conducting an analyte-specific detection reaction with the at least one reagent.

13. The method of claim 12, wherein the observing step includes visual observation.

14. The method of claim 12, wherein the observing step includes optical observation.

15. The method of claim 12, wherein the observing step includes the step of conducting a reflection photometric measurement.

* * * * *